United States Patent
Ashida et al.

(10) Patent No.: US 10,610,180 B2
(45) Date of Patent: Apr. 7, 2020

(54) X-RAY DIAGNOSTIC APPARATUS

(71) Applicants: Shinji Ashida, Yao-shi (JP); Toshiba Medical Systems Corporation, Otawara-shi (JP)

(72) Inventors: Shinji Ashida, Yao (JP); Satoru Ohishi, Otawara (JP)

(73) Assignees: Shinji Ashida, Yao-shi (JP); Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/707,198

(22) Filed: May 8, 2015

(65) Prior Publication Data

US 2015/0325011 A1 Nov. 12, 2015

(30) Foreign Application Priority Data

May 8, 2014 (JP) ................................. 2014-097161

(51) Int. Cl.
*G06K 9/00* (2006.01)
*A61B 6/00* (2006.01)
(Continued)

(52) U.S. Cl.
CPC .............. *A61B 6/504* (2013.01); *A61B 6/032* (2013.01); *A61B 6/035* (2013.01); *A61B 6/12* (2013.01); *A61B 6/4233* (2013.01); *A61B 6/4441* (2013.01); *A61B 6/466* (2013.01); *A61B 6/481* (2013.01); *A61B 6/5217* (2013.01);
(Continued)

(58) Field of Classification Search
CPC ............................................. G06T 2207/10116
See application file for complete search history.

(56) References Cited

U.S. PATENT DOCUMENTS

2005/0008115 A1* 1/2005 Tsukagoshi ............ A61B 6/032
378/4
2005/0084060 A1* 4/2005 Seppi ..................... A61B 6/032
378/5
(Continued)

FOREIGN PATENT DOCUMENTS

JP 2009-225 A 1/2009
JP 2010-88670 A 4/2010
(Continued)

OTHER PUBLICATIONS

McCollough (NPL "Strategies for Reducing Radiation Dose in CT", Jan. 2009; 47(1): 27-40. doi:10.1016/j.rcl.2008.10.006.). (Year: 2009).*
(Continued)

*Primary Examiner* — Oneal R Mistry
(74) *Attorney, Agent, or Firm* — Oblon, McClelland, Maier & Neustadt, L.L.P.

(57) ABSTRACT

An X-ray diagnostic apparatus according to an embodiment includes a support frame and processing circuitry. The support frame supports an X-ray generator and an X-ray detector. The processing circuitry is configured to, when rotational acquisitions are performed multiple times after a contrast agent is injected one time, previously set a generation condition of an X-ray that is generated by the X-ray generator for each of the rotational acquisitions, the rotational acquisitions being performed while the support frame is rotated around a subject.

20 Claims, 9 Drawing Sheets

(51) Int. Cl.
*G06T 11/00* (2006.01)
*A61B 6/03* (2006.01)
*H05G 1/30* (2006.01)
*G06T 15/08* (2011.01)
*A61B 6/12* (2006.01)

(52) U.S. Cl.
CPC ............ *A61B 6/542* (2013.01); *G06T 11/003* (2013.01); *G06T 15/08* (2013.01); *H05G 1/30* (2013.01); *G06T 2207/10116* (2013.01)

(56) References Cited

U.S. PATENT DOCUMENTS

| | | | | |
|---|---|---|---|---|
| 2007/0104317 | A1* | 5/2007 | Ohishi | A61B 6/481 378/98.12 |
| 2008/0056438 | A1* | 3/2008 | Zellerhoff | A61B 6/4441 378/11 |
| 2009/0010519 | A1* | 1/2009 | Wakai | G06F 19/321 382/131 |
| 2010/0310144 | A1* | 12/2010 | Chen | G06T 11/006 382/131 |
| 2011/0110488 | A1* | 5/2011 | Lardo | A61B 6/032 378/12 |
| 2011/0222750 | A1* | 9/2011 | Liao | A61B 6/4441 382/131 |
| 2012/0236995 | A1* | 9/2012 | Eusemann | A61B 6/03 378/108 |
| 2013/0211245 | A1* | 8/2013 | Vembar | A61B 6/032 600/428 |
| 2013/0308747 | A1* | 11/2013 | Abraham | A61B 6/03 378/16 |
| 2014/0254909 | A1* | 9/2014 | Carmi | A61B 6/032 382/131 |
| 2015/0139389 | A1* | 5/2015 | Eklund | A61B 6/06 378/62 |
| 2015/0190658 | A1* | 7/2015 | Yu | A61N 5/10 600/1 |
| 2016/0262712 | A1* | 9/2016 | Zhu | A61B 6/4014 |

FOREIGN PATENT DOCUMENTS

| | | |
|---|---|---|
| JP | 2010-167254 | 8/2010 |
| JP | 2010-193975 A | 9/2010 |
| WO | WO 2005/099566 A1 | 10/2005 |
| WO | 2007/074772 A1 | 7/2007 |

OTHER PUBLICATIONS

Japanese Office Action dated Mar. 12, 2019 in Japanese Patent Application No. 2015-095097, 3 pages.
Office Action dated Jan. 7, 2020 in Japanese Application No. 2015-095097.

* cited by examiner

FIG.3

(MASK IMAGE)

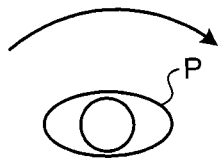

- ARM ROTATION: 60°/sec
- FRAME RATE: 60 fps
- 200 FRAMES

<X-RAY GENERATION CONDITION>
TUBE VOLTAGE: 100 kV
TUBE CURRENT: 250 mA
PULSE WIDTH: 12 msec
TUBE FOCUS SIZE: FOCUS MIDDLE (0.6 mm)
BEAM FILTER: Al 1.8 mm

(FIRST CONTRAST IMAGE)

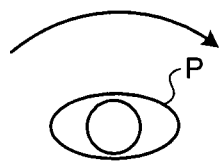

- ARM ROTATION: 60°/sec
- FRAME RATE: 60 fps
- 200 FRAMES

<X-RAY GENERATION CONDITION>
TUBE VOLTAGE: 100 kV
TUBE CURRENT: 250 mA
PULSE WIDTH: 12 msec
TUBE FOCUS SIZE: FOCUS MIDDLE (0.6 mm)
BEAM FILTER: Al 1.8mm

(SECOND CONTRAST IMAGE)

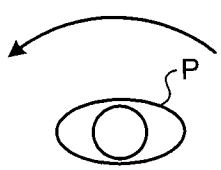

- ARM ROTATION: 60°/sec
- FRAME RATE: 60 fps
- 200 FRAMES

<X-RAY GENERATION CONDITION>
TUBE VOLTAGE: 100 kV
TUBE CURRENT: 250 mA
PULSE WIDTH: 6 msec
TUBE FOCUS SIZE: FOCUS MIDDLE (0.6 mm)
BEAM FILTER: Al 1.8 mm

FIG.5

(MASK IMAGE)

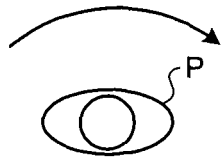

- ARM ROTATION: 60°/sec
- FRAME RATE: 60 fps
- 200 FRAMES

<X-RAY GENERATION CONDITION>
TUBE VOLTAGE: 100 kV
TUBE CURRENT: 250 mA
PULSE WIDTH: 12 msec
TUBE FOCUS SIZE: FOCUS MIDDLE (0.6 mm)
BEAM FILTER: Cu 0.2 mm

(FIRST CONTRAST IMAGE)

- ARM ROTATION: 60°/sec
- FRAME RATE: 60 fps
- 200 FRAMES

<X-RAY GENERATION CONDITION>
TUBE VOLTAGE: 100 kV
TUBE CURRENT: 250 mA
PULSE WIDTH: 12 msec
TUBE FOCUS SIZE: FOCUS MIDDLE (0.6 mm)
BEAM FILTER: Cu 0.2 mm

(SECOND CONTRAST IMAGE)

- ARM ROTATION: 60°/sec
- FRAME RATE: 60 fps
- 200 FRAMES

<X-RAY GENERATION CONDITION>
TUBE VOLTAGE: 80 kV
TUBE CURRENT: 250 mA
PULSE WIDTH: 12 msec
TUBE FOCUS SIZE: FOCUS MIDDLE (0.6 mm)
BEAM FILTER: Al 1.8 mm

FIG.6
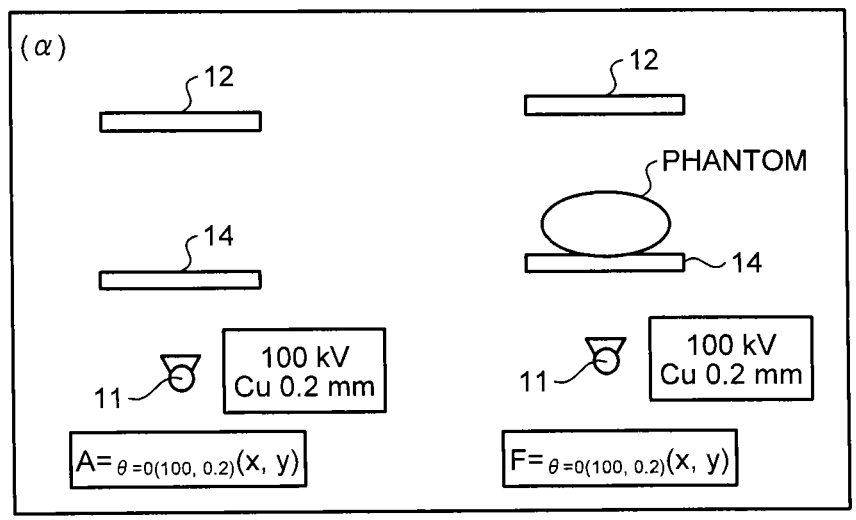
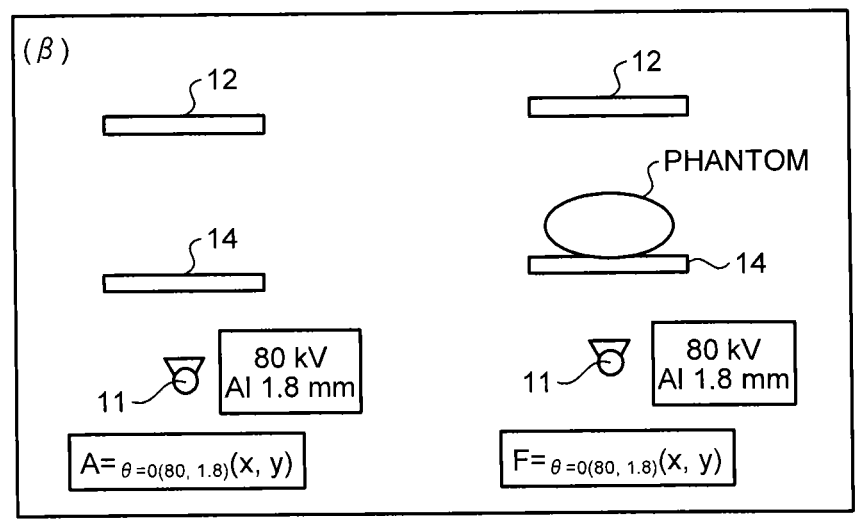

FIG.7
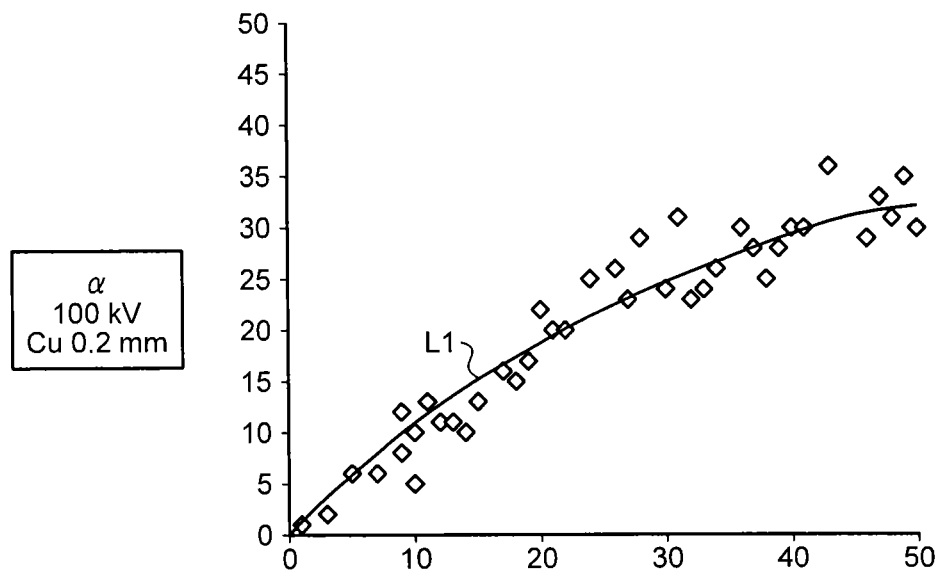
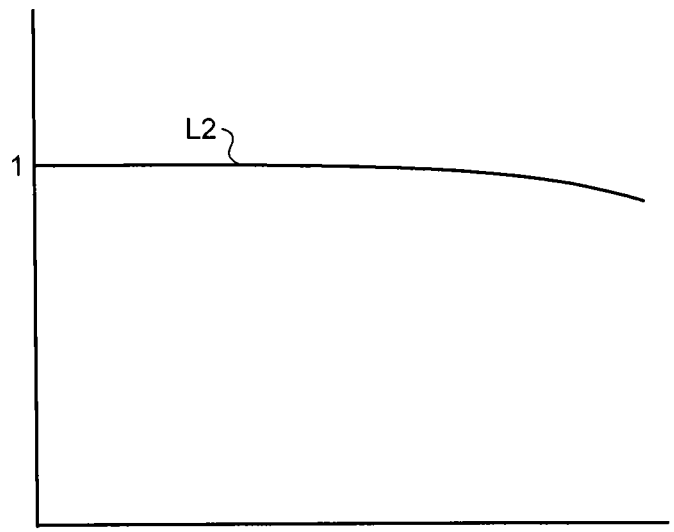

X-RAY DIAGNOSTIC APPARATUS

CROSS-REFERENCE TO RELATED APPLICATION

This application is based upon and claims the benefit of priority from Japanese Patent Application No. 2014-097161, filed on May 8, 2014, the entire contents of all of which are incorporated herein by reference.

FIELD

Embodiments described herein relate generally to an X-ray diagnostic apparatus.

BACKGROUND

There is a conventionally-known technology of X-ray diagnostic apparatuses for performing rotational acquisition multiple times after a contrast agent is injected and reconstructing a three-dimensional image from image data that is acquired during each rotational acquisition. For example, with the above-described technology, after a contrast agent is injected, rotational acquisitions are performed multiple times to acquire projection data at a predetermined frame rate while an arm that supports an X-ray generator and an X-ray detector is rotated, and three-dimensional volume data is reconstructed from the projection data that is acquired during each rotational acquisition. Thus, with the above-described technology, acquisitions (for example, an acquisition during CT-like imaging of hepatic arteriography for a diagnosis of a hepatic tumor and the following acquisition during CT-like imaging at a later phase (alternatively, an acquisition of corona enhancement around a hepatocellular tumor)) at multiple time phases can be performed during one-time contrast injection, and invasiveness for patients by imaging can be reduced. However, with the above-described conventional technology, it is sometimes difficult to acquire the optimum image data during each rotational acquisition.

BRIEF DESCRIPTION OF THE DRAWINGS

FIG. 3 is a diagram that illustrates an example of a rotational acquisition of the X-ray diagnostic apparatus according to the first embodiment;

FIG. 5 is a diagram that illustrates an example of an acquisition by using correction data according to a modified example 5;

FIG. 6 is a diagram that illustrates an example of generation of correction data according to the modified example 5;

FIG. 7 is a diagram that illustrates an example of correction data according to the modified example 5.

DETAILED DESCRIPTION

With reference to the drawings, a detailed explanation is given below of an X-ray diagnostic apparatus according to an embodiment. Furthermore, there is no limitation on the embodiment that is described below.

The X-ray diagnostic apparatus according to the embodiment includes a support frame and processing circuitry. The support frame supports an X-ray generator and an X-ray detector. The processing circuitry is configured to, when rotational acquisitions are performed multiple times after a contrast agent is injected one time, previously set a generation condition of an X-ray that is generated by the X-ray generator for each of the rotational acquisitions.

First Embodiment

Figure 1:
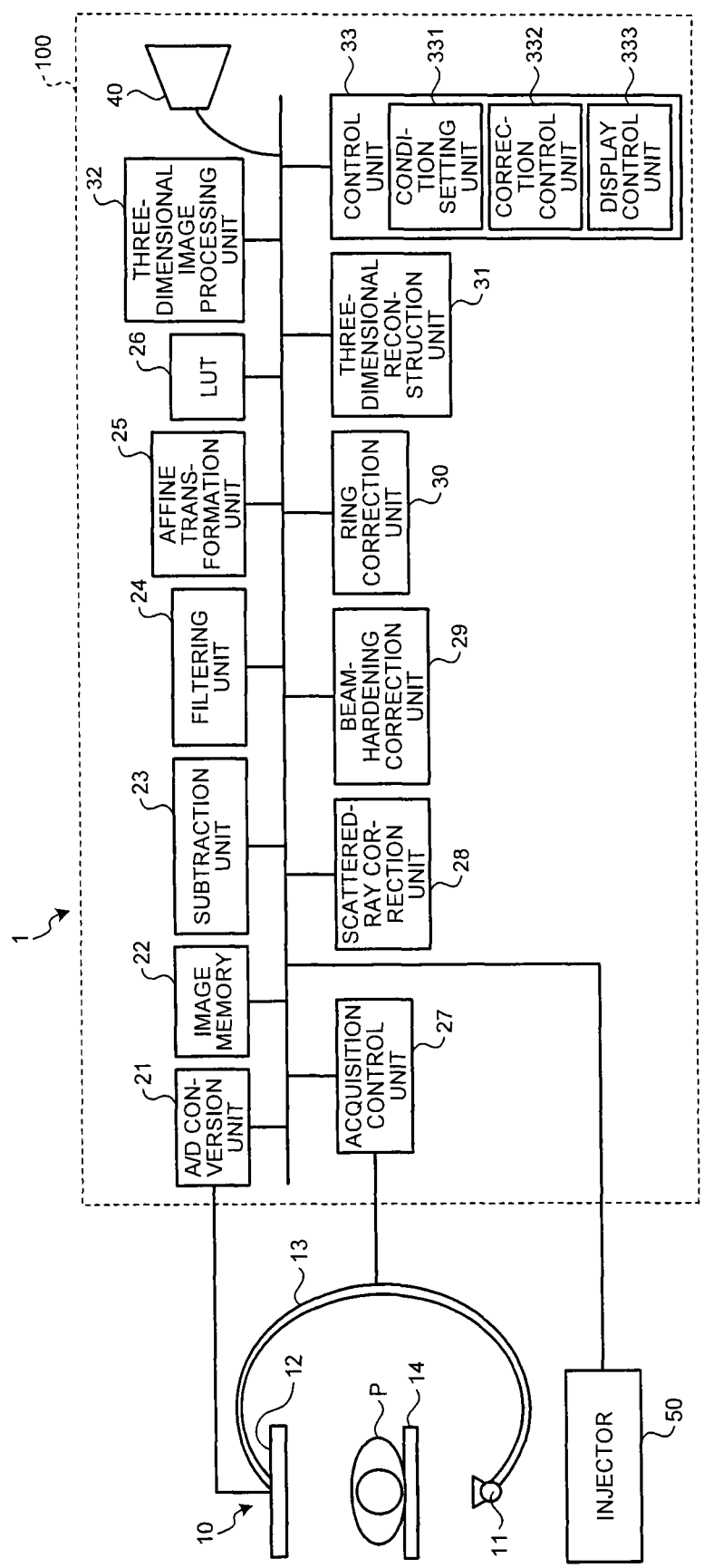
FIG. 1 is a diagram that illustrates an example of the configuration of an X-ray diagnostic apparatus according to a first embodiment.

FIG. 1 is a diagram that illustrates an example of the configuration of an X-ray diagnostic apparatus 1 according to a first embodiment. As illustrated in FIG. 1, the X-ray diagnostic apparatus 1 according to the first embodiment includes an X-ray acquisition mechanism 10 and an image processing device 100. The X-ray acquisition mechanism 10 includes an X-ray generator 11, an X-ray detector (Flat Panel Detector (FPD)) 12, a C-shaped arm 13, and a bed 14, and it is connected to an injector 50.

The injector 50 is a device for injecting a contrast agent through a catheter that is inserted into a subject P. Here, there may be cases in which an injection of a contrast agent from the injector 50 is started in accordance with an injection start command that is received via the image processing device 100 that is described later or in accordance with an injection start command that is directly input to the injector 50 by an operator.

The C-shaped arm 13 supports the X-ray generator 11 and the X-ray detector 12, and it is rotated by a motor that is provided on a support frame (not illustrated) at high speed like a propeller around the subject P that lies on the bed 14. Here, the C-shaped arm 13 is supported such that it is rotatable with respect to the XYZ axes that are the three axes that run at right angles to one another, and it is rotated by an undepicted driving unit with respect to each of the axes individually. X-ray generator 11 is a device that includes an X-ray tube and an X-ray movable diaphragm and generates X-rays through a high voltage supplied from the X-ray high-voltage generating unit. The X-ray tube applies X-rays. The X-ray movable diaphragm narrows the range of the X-rays applied from the X-ray tube to the subject P to a range containing a region of interest of the subject P.

As illustrated in FIG. 1, the image processing device 100 includes an Analog/Digital (A/D) conversion unit 21, an image memory 22, a subtraction unit 23, a filtering unit 24, an affine transformation unit 25, a Look Up Table (LUT) 26, an acquisition control unit 27, a scattered-ray correction unit 28, a beam-hardening correction unit 29, a ring correction unit 30, a three-dimensional reconstruction unit 31, a three-dimensional image processing unit 32, a control unit 33, and a display unit 40. Furthermore, although not illustrated, the image processing device 100 includes an input unit, such as a mouse, keyboard, trackball, or pointing device, to receive various operations on the X-ray diagnostic apparatus 1 from an operator.

The display unit 40 displays various images that are processed by the image processing device 100 or various types of information, such as a Graphical User Interface (GUI). For example, the display unit 40 is a Cathode Ray Tube (CRT) monitor or a liquid crystal monitor. The A/D conversion unit 21 is connected to the X-ray detector 12, and it converts an analog signal input from the X-ray detector 12 into a digital signal and stores the converted digital signal as an X-ray acquisition image in the image memory 22. The image memory 22 stores the X-ray acquisition image (projection data). Furthermore, the image memory 22 stores reconstruction data (volume data) that is reconstructed by the three-dimensional reconstruction unit 31 that is described later or three-dimensional images that are generated by the three-dimensional image processing unit 32.

The subtraction unit 23 generates a subtraction image, such as a Digital Subtraction Angiography (DSA) image. For example, the subtraction unit 23 generates a DSA image by using mask images and contrast images that are stored in the image memory 22 or generates a three-dimensional blood vessel image by using mask volume data that is reconstructed from mask images and contrast volume data that is reconstructed from contrast images. Here, under the control of the control unit 33 that is described later, the subtraction unit 23 generates a DSA image or a three-dimensional blood vessel image by using mask image and contrast image.

The filtering unit 24 performs a high-pass filtering, a low-pass filtering, or the like. The affine transformation unit 25 makes an enlargement, minification, movement, or the like, of images. The LUT 26 performs a tone conversion. The scattered-ray correction unit 28 performs a scattered-ray correction to remove scattered ray components that are included in a mask image and a contrast image. The beam-hardening correction unit 29 performs a beam hardening correction by using a correction table on the basis of the thickness of soft tissues, or the thickness of soft tissues and the thickness of a bone area. The ring correction unit 30 performs a ring correction to remove ring-shaped artifacts due to the unevenness of gains of the X-ray detector 12, or the like.

Under the control of the control unit 33 that is described later, the acquisition control unit 27 controls various operations related to acquisition of the X-ray acquisition mechanism 10. For example, the acquisition control unit 27 controls rotational acquisition for acquiring projection data at a predetermined frame rate while the C-shaped arm 13 is rotated. For example, by using, as a trigger, a signal that is output at the start of an injection of a contrast agent from the injector 50, the acquisition control unit 27 controls multiple rotational acquisitions after a contrast agent is injected one time. In other words, rotational acquisitions are automatically performed multiple times after a contrast agent is injected once. Here, the acquisition control unit 27 controls the start of multiple rotational acquisitions by using the elapsed time from a start of injection, thereby performing each rotational acquisition in synchronization with the time in which a contrast agent reaches a target for the rotational acquisition.

Furthermore, while the C-shaped arm 13 is controlled so as to rotate, the acquisition control unit 27 controls an undepicted high-voltage generating unit so as to generate X-rays continuously with the X-ray generator 11 or intermittently and controls the X-ray detector 12 so as to detect X-rays that are transmitted through the subject P. Here, the acquisition control unit 27 generates X-rays on the basis of the X-ray generation condition that is set for each rotational acquisition by the control unit 33 that is described later.

The three-dimensional reconstruction unit 31 reconstructs reconstruction data (volume data) from projection data that is acquired during a rotational acquisition with the X-ray acquisition mechanism 10. For example, the three-dimensional reconstruction unit 31 reconstructs volume data from post-subtraction projection data that is stored in the image memory 22 after the subtraction unit 23 performs a subtraction of mask images and corresponding contrast images. Alternatively, the three-dimensional reconstruction unit 31 reconstructs mask and contrast volume data from projection data that is stored in the image memory 22 after the A/D conversion unit 21 performs a digital data conversion. Then, the three-dimensional reconstruction unit 31 stores the reconstructed volume data in the image memory 22.

The three-dimensional image processing unit 32 generates a three-dimensional image from volume data that is stored in the image memory 22. For example, the three-dimensional image processing unit 32 generates a volume rendering image or a Multi Planar Reconstruction (MPR) image from volume data. Then, the three-dimensional image processing unit 32 stores the generated three-dimensional image in the image memory 22.

The control unit 33 performs overall control of the X-ray diagnostic apparatus 1. Specifically, the control unit 33 controls various operations related to the acquisition of X-ray images by the X-ray acquisition mechanism 10, the generation of a various images, the display of those images by the display unit 40, or the like. For example, the control unit 33 controls the rotational acquisition of the X-ray acquisition mechanism 10, the generation of a three-dimensional image from projection data that is acquired during the rotational acquisition, and the display of rendering images on the display unit 40. Here, for example, as illustrated in FIG. 1, the control unit 33 includes a condition setting unit 331, a correction control unit 332, and a display control unit 333, and it controls the X-ray generation condition for each rotational acquisition, thereby enabling acquisition of the optimum image data during each rotational acquisition.

As described above, in conventional X-ray diagnostic apparatuses, after a contrast agent is injected, rotational acquisitions are performed multiple times, and a three-dimensional image is generated from projection data that is acquired during each rotational acquisition, whereby it is possible to reduce patients' invasiveness during imaging. However, in conventional X-ray diagnostic apparatuses, after a contrast agent is injected, multiple rotational acquisitions are performed by using the same X-ray generation condition; therefore, it is sometimes difficult to acquire the optimum image data during each rotational acquisition.

For example, when rotational acquisitions are performed twice after a contrast agent is injected once, if a contrast agent signal that is acquired during the second acquisition is extremely weaker than a contrast agent signal that is acquired during the first acquisition, and if the second acquisition is performed with the same condition of the first acquisition, the dose during the second acquisition is insufficient; therefore, it is difficult to separate noise and signals, and it is difficult to correctly observe the object of interest. Furthermore, for example, when rotational acquisitions are performed twice after a contrast agent is injected once, if detailed structure is required at the first acquisition while broad structure is required at the second acquisition, and if the second acquisition is performed with the same condition of the first acquisition, the dose during the second acquisition is excessive.

Therefore, in the X-ray diagnostic apparatus 1 according to the present embodiment, the above-described control unit 33 controls the X-ray generation condition for each rotational acquisition so that it is possible to acquire the optimum image data during each rotational acquisition. Specifically, if rotational acquisitions are performed multiple times after a contrast agent is injected once, the condition setting unit 331 previously sets, for each rotational acquisition, the generation condition of X-rays that are generated by the X-ray generator 11. For example, the condition setting unit 331 previously sets at least one of the tube voltage, the tube current, the pulse width, the X-ray tube focus size, and the beam filter as the X-ray generation condition for each rotational acquisition.

The correction control unit 332 corrects data that is acquired by the X-ray detector 12 in accordance with the X-ray generation condition that is set by the condition setting unit 331. Specifically, if a subtraction operation is performed by using mask images and corresponding contrast images that are acquired under the different generation conditions, the correction control unit 332 corrects the projection data such that the subtraction operation is performed on the sets of projection data for which the generation conditions are matched.

The display control unit 333 controls the display unit 40 to display multiple rendering images created from multiple three-dimensional images that are taken during rotational acquisitions under the X-ray generation conditions that are set by the condition setting unit 331.

Figure 2:
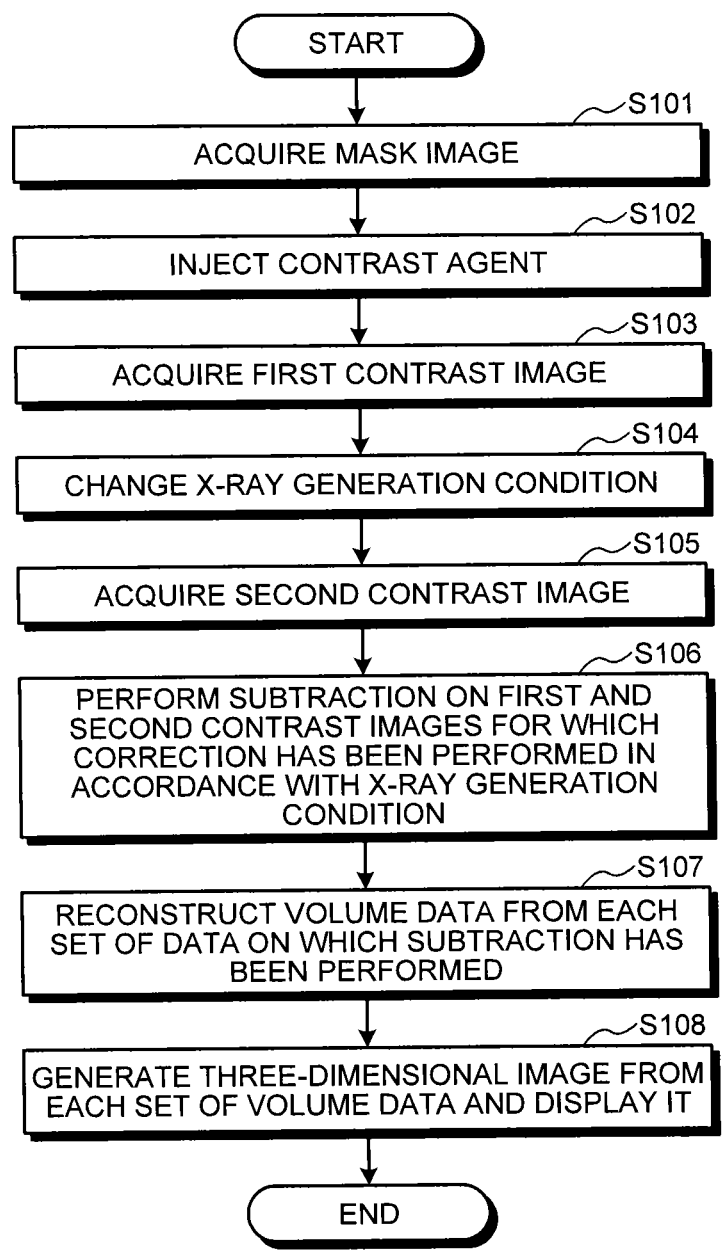
FIG. 2 is a flowchart that illustrates an example of the steps of the operation of the X-ray diagnostic apparatus according to the first embodiment.

An explanation is given below, with reference to FIG. 2, of an example of the operation of the X-ray diagnostic apparatus 1 according to the present embodiment. FIG. 2 is a flowchart that illustrates an example of the steps of the operation of the X-ray diagnostic apparatus 1 according to the first embodiment. Furthermore, FIG. 2 illustrates a case where, before a contrast agent is injected, a rotational acquisition is performed for mask images and, after the contrast agent is injected, rotational acquisitions are performed twice.

As illustrated in FIG. 2, in the X-ray diagnostic apparatus 1, before a contrast agent is injected, mask images are acquired during a rotational acquisition at first (Step S101). Specifically, in the X-ray diagnostic apparatus 1, the acquisition control unit 27 controls the X-ray acquisition mechanism 10 so as to acquire projection data at a predetermined frame with the X-ray generation conditions that are set by the condition setting unit 331. Furthermore, projection data for mask images are converted into digital signals by the A/D conversion unit 21 and is stored in the image memory 22.

After acquisition of mask images are completed, the injector 50 injects a contrast agent into the subject P (Step S102). After the contrast agent is injected, and after a predetermined time (a first elapsed time) elapses, the acquisition control unit 27 acquires the first contrast images by a rotational acquisition with the X-ray generation conditions that are set by the condition setting unit 331 (Step S103). Here, the condition setting unit 331 changes the X-ray generation conditions for acquiring the second contrast images (Step S104).

Then, after the second elapsed time that is longer than the first elapsed time elapses after the contrast agent is injected, the acquisition control unit 27 acquires the second contrast images during a rotational acquisition with the X-ray generation conditions that are changed by the condition setting unit 331 (Step S105). Here, the condition setting unit 331 changes at least one of the tube voltage, the tube current, the pulse width, the X-ray tube focus size, and the beam filter as the X-ray generation conditions for each rotational acquisition. FIG. 3 is a diagram that illustrates an example of the rotational acquisition of the X-ray diagnostic apparatus 1 according to the first embodiment. Here, FIG. 3 illustrates, for example, a case where the mask images and the first contrast images are acquired under the same X-ray generation condition and the pulse width of X-rays that are generated by the X-ray generator 11 is changed for the second contrast images.

For example, in the X-ray diagnostic apparatus 1, as illustrated in FIG. 3, during the mask image acquisition that is equivalent to Step S101 of FIG. 2, the C-shaped arm 13 is rotated (forward) at 60 degrees per second (arm rotation speed: 60°/sec), while the projections are acquired at fixed frame rate (frame rate: 60 fps), and the mask image of 200 frames is gotten at an interval of 1 degree. Here, the condition setting unit 331 sets the X-ray generation condition "the tube voltage: 100 kV", "the tube current: 250 mA", "the pulse width: 12 msec", "the tube focus size: Focus Middle (0.6 mm)", and "the beam filter: Al 1.8 mm". The acquisition control unit 27 causes the mask image of 200 frames to be acquired under the above-described X-ray generation condition that is set by the condition setting unit 331. The acquired mask image of 200 frames is converted into digital signals by the A/D conversion unit 21 and is stored in the image memory 22.

After the mask image is acquired, the C-shaped arm 13 is returned (rotated backward) to the initial rotation start position at high speed 60 degrees per second. Next, a contrast agent is injected by the injector 50 and, after a certain period of time elapses, during the first contrast image acquisition that is equivalent to Step S103 of FIG. 2, the C-shaped arm 13 is rotated (forward) at 60 degrees per second (arm rotation: 60°/sec), the projections are acquired at a fixed frame rate (frame rate: 60 fps), and the first contrast image of 200 frames is gotten at an interval of 1 degree. Here, the condition setting unit 331 sets the same X-ray generation condition with that for the mask image acquisition. Specifically, the acquisition control unit 27 causes the first contrast image of 200 frames to be acquired with "the tube voltage: 100 kV", "the tube current: 250 mA", "the pulse width: 12 msec", "the tube focus size: Focus Middle (0.6 mm)", and "the beam filter: Al 1.8 mm". The acquired first contrast image of 200 frames is converted into digital signals by the A/D conversion unit 21 and is stored in the image memory 22.

After the first contrast image is acquired, and after a specific time (the time that is different from the first time) elapses after the start of imaging, during the second contrast image acquisition that is equivalent to Step S105 of FIG. 2, the C-shaped arm 13 is rotated (backward) at 60 degrees per second (arm rotation: 60°/sec), the projections are acquired at a fixed frame rate (frame rate: 60 fps), and the second contrast image of 200 frames is gotten at an interval of 1 degree. Here, the condition setting unit 331 changes the X-ray generation condition for acquiring the second contrast image (an equivalent of Step S104 of FIG. 2). For example, the condition setting unit 331 changes "the pulse width" from "12 msec" to "6 msec" for acquiring the second contrast image. Specifically, the acquisition control unit 27 causes the second contrast image of 200 frames to be acquired with "the tube voltage: 100 kV", "the tube current: 250 mA", "the pulse width: 6 msec", "the tube focus size: Focus Middle (0.6 mm)", and "the beam filter: Al 1.8 mm". Specifically, the condition setting unit 331 sets the X-ray generation condition such that, out of the rotational acquisitions that are performed multiple times, the total amount of X-ray radiation during the second rotational acquisition, which is performed after the first rotational acquisition, is nearly equal to or less than ½ of the total amount of X-ray radiation during the first rotational acquisition. The acquired second contrast image of 200 frames is converted into digital signals by the A/D conversion unit 21 and is stored in the image memory 22.

As described above, the X-ray diagnostic apparatus 1 acquires the first contrast image and the second contrast image for which, for example, the "pulse width" is changed. With reference back to FIG. 2, after the second contrast image is acquired at Step S105, the subtraction unit 23 performs a subtraction on the first contrast image and the second contrast image for which a correction has been performed in accordance with the X-ray generation condition under the control of the correction control unit 332 (Step S106). Here, if a subtraction operation is performed on projection data on the mask image and projection data on the contrast image that are acquired under the different generation conditions, the correction control unit 332 corrects the projection data such that the subtraction operation is performed on the sets of projection data for which the generation conditions are matched.

For example, the correction control unit 332 causes a subtraction operation to be performed on the mask image and the first contrast image that are acquired under the X-ray generation conditions illustrated in FIG. 3 by using the following Equation (1) and causes a subtraction operation to be performed on the mask image and the second contrast image that are acquired under the X-ray generation condition illustrated in FIG. 3 by using the following Equation (2). Here, $DSA_\theta(x, y)$, $MASK_\theta(x, y)$, $CONT1_\theta(x, y)$, and $CONT2_\theta(x, y)$ in Equation (1) and Equation (2) represent subtraction data, the mask image, the first contrast image, and the second contrast image. Furthermore, "θ" in Equation (1) and Equation (2) represents the rotation angle.

$$DSA_\theta(x, y) = \log_e\left(-\frac{CONT1_\theta(x, y)}{MASK_\theta(x, y)}\right) \quad (1)$$

$$DSA_\theta(x, y) = \log_e\left(-\frac{2 \times CONT2_\theta(x, y)}{MASK_\theta(x, y)}\right) \quad (2)$$

For example, if a subtraction operation is performed on the mask image and the first contrast image for which the X-ray generation conditions are the same, the subtraction operation is performed without a correction by the correction control unit 332. Specifically, as represented by Equation (1), the subtraction unit 23 reads, from the image memory 22, the mask image of 200 frames and the first contrast image of 200 frames and performs a subtraction (Log subtraction) by using projection data of the corresponding rotation angle, thereby generating subtraction data for the first contrast image.

Furthermore, if a subtraction operation is performed on the mask image and the second contrast image for which the X-ray generation conditions are different, the subtraction operation is performed after the correction control unit 332 performs a correction. For example, as illustrated in FIG. 3, if a subtraction is performed on the mask image that is acquired with "the pulse width: 12 msec" and the second contrast image that is acquired with "the pulse width: 6 msec", the subtraction unit 23 generates subtraction data for the second contrast image by using the equation in which the second contrast image is multiplied by the correction factor "2" as represented by Equation (2). Specifically, the subtraction unit 23 reads, from the image memory 22, the mask image of 200 frames and the second contrast image of 200 frames and performs a subtraction by using projection data of the corresponding rotation angle by using Equation (2), thereby generating subtraction data for the second contrast image.

As described above, with regard to a change in the tube current and the pulse width for which the amount of X-rays is linearly changed, the correction control unit 332 controls the subtraction unit 23 so as to determine a correction factor to compensate for the change and perform a subtraction using the determined correction factor. Furthermore, an explanation is given in FIG. 2 of a case where a subtraction is performed after the second contrast image is acquired; however, there is no limitation on the embodiment and, for example, there may be a case where subtraction data on the first contrast image is generated while the second contrast image is acquired.

After sets of subtraction data on the first contrast image and the second contrast image are generated at Step S106, each set of subtraction data is transmitted to the three-dimensional reconstruction unit 31 so that volume data is generated. Specifically, the three-dimensional reconstruction unit 31 reconstructs volume data from each set of data on which a subtraction has been performed (Step S107). For example, the three-dimensional reconstruction unit 31 reconstructs volume data by using a filtered backprojection method that is proposed by Feldkamp et al.

In such a case, the three-dimensional reconstruction unit 31 applies an appropriate convolution filter of Shepp & Logan, Ramachandran, or the like, to subtraction data for the first contrast image and then performs a back projection calculation, thereby reconstructing volume data. Furthermore, as the area of interest in the second contrast image does not need much high spatial resolution, the three-dimensional reconstruction unit 31 applies, to the subtraction data for the second contrast image, for example, a convolution filter that has a further weaker spatial enhancement compared to the filter that is used for the reconstruction of the first contrast image and then performs a back projection calculation, thereby reconstructing volume data.

Here, a reconstruction area is defined as a cylinder that is inscribed in a bundle of X-rays from the X-ray generator 11 in all directions during rotational acquisition. For example, the inside of the cylinder is made discrete in three dimensions by the length "d" at the central portion of a reconstruction area that is projected onto the width of a single detection element of the X-ray detector 12, and a reconstruction image is obtained from data on the discrete points. Furthermore, although an example of the discrete interval is illustrated here, this is sometimes different depending on apparatuses and manufacturers; therefore, basically, it is appropriate to use the discrete interval that is defined by the apparatus. Moreover, there may be a case where a reconstruction is performed by using iterative reconstruction algorithms, such as an Algebraic Reconstruction Algorithm (ART) method, an Expectation Maximization (EM) method, or a Total Variation (TV) method. The volume data that is reconstructed by the three-dimensional reconstruction unit 31 as described above is stored in the image memory 22.

After the volume data is reconstructed at Step S107, the three-dimensional image processing unit 32 generates rendering images from the reconstructed volume data, and the display control unit 333 displays the generated rendering images on the display unit 40 (Step S108). For example, the three-dimensional image processing unit 32 generates volume rendering images or MPR images from volume data as described above. Here, the display control unit 333 fuses generated volume rendering images or MPR images for a display, or displays rendering images in different colors.

An explanation is given above of an example of the operation performed by the X-ray diagnostic apparatus 1 according to the first embodiment. In the above-described example, an explanation is given of a case where the pulse width for acquiring the second contrast image is shorter than the pulse width for acquiring the first contrast image so that the amount of X-rays for the second contrast image is smaller than that for the first contrast image. This embodiment is applied to acquisitions of, for example, hepatic arteries, portal veins, or arteries of the brain. For example, proper hepatic arteries, portal veins, internal carotid arteries, vertebral arteries, or the like, are acquired with the first contrast image, and corona enhancement, hepatic veins, veins of the brain, capillary blood vessels, or the like, are acquired with the second contrast image. In such a case, if a rotational acquisition is performed on an arterial phase of the subject P, the condition setting unit 331 sets the X-ray generation conditions such that the amount of X-rays is increased compared to the other phases and, if a rotational acquisition is performed on a capillary blood vessel phase or a venous phase of the subject P, it sets the X-ray generation condition such that the amount of X-rays is decreased compared to the other phases.

Figure 4:
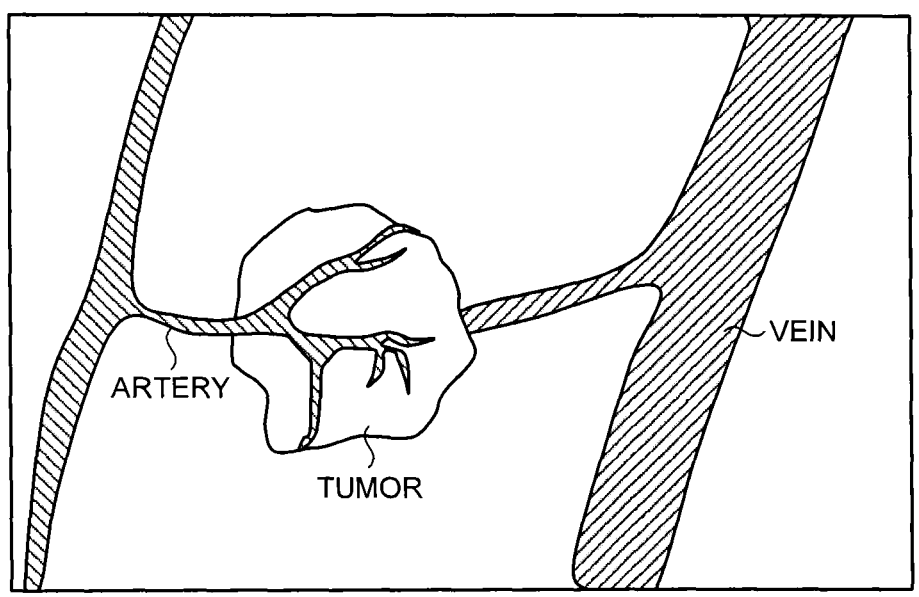
FIG. 4 is a diagram that illustrates an example of a display image according to the first embodiment.

The X-ray diagnostic apparatus 1 conducts rotational acquisitions multiple times as described above so that it can acquire the optimum image data during each rotational acquisition. For example, if region of interest for the first acquisition has a detailed structure while region of interest for the second acquisition has a broad structure, the X-ray diagnostic apparatus 1 can prevent an unnecessary increase in the exposed dose due to the overmuch dose during the second acquisition and can provide the optimum image for an observation. For example, this embodiment is applied to acquisition in the case of an identification of a feeding artery for supplying nutrients and oxygen to a tumor in addition to an identification of a tumor. For example, as illustrated in FIG. 4, the X-ray diagnostic apparatus 1 can visualize a narrow artery (feeding artery) that is newly grown in accordance with the formation of a tumor as the first contrast image, visualize a vein as the second contrast image, and then fuse them to obtain a colored display image of different colors (e.g., coloring of an artery in red, a vein in blue, or the like), and display it on the display unit 40 as an easily observed image. Thus, for example, it is possible to operate a catheter on the basis of the information on a feeding artery. Furthermore, FIG. 4 is a diagram that illustrates an example of a display image according to the first embodiment.

Furthermore, this embodiment is applied to visualizing for identifying a disease site in detail when there is disease, such as an aneurysm, in arteries of the brain, or the like. For example, it is applicable to brain surgery for cerebral aneurysm or an arteriovenous malformation that is a connection between arteries and veins via a nidus. More specifically, when brain surgery is conducted, it is often considered that the information on an artery that is the therapeutic objective is all that is needed. However, when brain surgery is conducted, it is desirable that the area of removed skull is smaller. Here, if veins are overlapped in the surgery site where the amount of removed skull is small, there is a need to find another approach so as to prevent damages to the veins, which results in an increase in the burden on a patient. Therefore, for brain surgery, arteries and veins are sometimes captured to avoid previous potential risks. In such a case, the condition setting unit 331 makes, for example, the pulse width for acquiring a vein as the second contrast image narrower than the pulse width for acquiring an artery as the first contrast image.

Furthermore, this embodiment is applicable to a case where, for example, if there is a need to determine whether there is no infarct, an artery is visualized as the first contrast image and a capillary blood vessel is visualized as the second contrast image. In such a case, the condition setting unit 331 makes, for example, the pulse width for acquiring a capillary blood vessel as the second contrast image narrower than the pulse width for acquiring an artery as the first contrast image.

Modified Example 1

In the above-described embodiment, an explanation is given of a case where the amount of X-rays for the second contrast image is smaller than that for the first contrast image; however, there is no limitation on the embodiment, and there may be a case where the amount of X-rays for the second contrast image is larger than that for the first contrast image. For example, if the detailed blood vessel structure, or the like, is unnecessary for arteries and it is only necessary to know the rough blood vessel structure, the amount of X-rays is reduced to prevent unnecessary radiation exposure. However, the density of a contrast agent in capillary blood vessels or veins is lower than that in arteries; therefore, if capillary blood vessels or veins with low contrast agent signals need to be displayed with a certain spatial resolution in spite of noise (if there is a need for an observation in more detail compared to a spatial resolution for capillary blood vessels or veins although it is slightly poorer spatial resolution for arteries in the above-described example), the amount of X-rays for the second contrast image is made larger than that for the first contrast image. For example, the modified example 1 is applied to acquisition such as CT-like imaging that is performed during hepatic arteriography in the case of a diagnosis for a hepatocellular tumor. During the acquisition of an earlier phase in a CT-like imaging, a hepatocellular tumor is highly contrasted, and therefore a hepatocellular tumor can be identified with a small amount of X-rays. Thus, the condition setting unit 331 reduces the amount of X-rays during the acquisition of an earlier phase in a CT-like imaging. Conversely, during the acquisition of a later phase in a CT-like imaging, an image (corona enhancement) of a contrast agent remained at around a hepatocellular tumor is observed. With regard to the corona enhancement, the contrast is weaker compared to the enhancement of hepatocellular tumor at earlier phase. Therefore, the condition setting unit 331 sets a larger amount of X-rays during the acquisition of a later phase compared to the acquisition of an earlier phase. Furthermore, the corona enhancement is not observed for other than hepatocellular tumors and, if this enhancement is observed, a hepatocellular tumor is suggested with higher percentage.

Furthermore, the above-described modified example 1 is also applied to an acquisition during a treatment for which reference information is obtained with regard to an arterial phase in which a catheter is just passed through after the catheter is inserted through a vein. In such a case, the condition setting unit 331 sets a larger amount of X-rays for acquiring a venous phase as the second contrast image compared to that for acquiring an arterial phase as the first contrast image.

In such a case, for example, contrary to the above-described case, the first contrast image is acquired with "the tube voltage: 100 kV", "the tube current: 250 mA", "the pulse width: 6 msec", "the tube focus size: Focus Middle (0.6 mm)", and "the beam filter: Al 1.8 mm", and the second contrast image is acquired with "the tube voltage: 100 kV", "the tube current: 250 mA", "the pulse width: 12 msec", "the tube focus size: Focus Middle (0.6 mm)", and "the beam filter: Al 1.8 mm". Specifically, the condition setting unit 331 sets the X-ray generation condition such that, with regard to the rotational acquisitions that are performed multiple times, the total amount of X-ray radiation during the second rotational acquisition, which is performed after the first rotational acquisition, is nearly equal to or more than twice the total amount of X-ray radiation during the first rotational acquisition. Furthermore, in this case, the correction factor "2" for the X-ray generation condition difference is inserted into Equation (1), and the correction factor "2" is removed from Equation (2).

Modified Example 2

Furthermore, in the above-described embodiment, an explanation is given of a case where a subtraction image is reconstructed. However, there is no limitation on the embodiment and, for example, there may be a case where a subtraction is performed after reconstruction. In such a case, if a subtraction operation is performed on sets of reconstruction data that is reconstructed from sets of projection data such as a mask image and contrast images that are acquired under different generation conditions, the correction control unit 332 corrects the reconstruction data such that the subtraction operation is performed by using the sets of reconstruction data for which the generation conditions are matched.

For example, the three-dimensional reconstruction unit 31 reads projection data of the mask image, the first contrast image, and the second contrast image from the image memory 22 and reconstructs volume data individually. Then, the subtraction unit 23 performs a subtraction of reconstructed volume data reconstructed from the mask image and each of the contrast images. Here, the subtraction unit 23 performs a subtraction by using data that is corrected by using a correction factor that is determined by the correction control unit 332.

As described above, as a subtraction is performed after reconstruction, artifacts due to misregistration can be removed. For example, if the rotation direction of the C-shaped arm 13 for acquiring a mask image is different from the rotation direction of the C-shaped arm 13 for acquiring a contrast image, there is a possibility of the occurrence of misregistration at an edge portion even with the same angle due to the difference in the rotation direction. Therefore, a reconstruction is first performed so that the positional deviation during acquisitions is corrected for each rotational acquisition, and artifacts due to misregistration are removed.

Modified Example 3

Furthermore, in the above-described embodiment, an explanation is given of a case where the mask image is acquired and a subtraction is performed by using the first contrast image and the second contrast image. However, there is no limitation on the embodiment, and there may be a case where the mask image is not acquired but only the first contrast image and the second contrast image are acquired. In such a case, the density of a contrast agent is changed or various correction operations are performed in accordance with a purpose. For example, if only blood vessels are interested in the density of a contrast agent is increased, and the first contrast image and the second contrast image are acquired with respect to blood vessels that are imaged at different timings after the contrast agent is injected. In this case, signals due to a contrast agent are strong; therefore, there may be a case where a scattered-ray correction, or the like, for removing scattered rays is not performed.

Furthermore, for example, if both blood vessels and soft tissues are interested in, a low-density contrast agent is injected to prevent artifacts come from strong signals for soft tissues observation, and the first contrast image and the second contrast image are acquired. In this case, as signals due to a contrast agent are weak, a scattered-ray correction, a subtraction for a correction image for correcting density non-uniformity, and a beam hardening correction are performed on the first contrast image and the second contrast image. Afterward, the three-dimensional reconstruction unit 31 performs reconstruction of volume data. Furthermore, there may be a case where a ring correction is performed in addition to the above-described corrections.

Modified Example 4

Furthermore, in the above-described embodiment, an explanation is given of a case where images are acquired with the same tube focus size. However, there is no limitation on the embodiment, and there may be a case where the tube focus size is changed. For example, if acquisition is performed under the X-ray generation condition in which the amount of X-rays is small, a relative noise level is increased; however, if the target is a vein, or the like, lower spatial resolution may be acceptable and, if a reconstruction is performed by using a filter with a low degree of spatial enhancement, a smooth image with reduced noise is generated. Here, if the tube focus size is increased, an image becomes blurred, and noise is relatively reduced; therefore, it is possible to obtain the same effect as that of a reconstruction using a filter with a low degree of spatial enhancement. For example, the same effect is expected in a case where the image acquired with the tube focus size "0.6 mm" is reconstructed by using a filter with a low degree of spatial enhancement and in a case where the image acquired with the tube focus size "1.0 mm" is reconstructed by using a filter with a high degree of spatial enhancement. Therefore, for example, if the second contrast image is acquired under the X-ray generation condition in which the amount of X-rays is small, the correction control unit 332 can perform a control so as to generate a smooth image by simultaneously increasing the tube focus size.

Modified Example 5

Furthermore, in the above-described embodiment, an explanation is given of a case where images are acquired with the same tube voltage and beam filter. However, there is no limitation on the embodiment, and there may be a case where the tube voltage or the beam filter is changed. Here, if the tube voltage or the beam filter is changed, the radiation quality of X-rays is changed; therefore, instead of the above-described linear correction, a correction is performed by using correction data with all the combinations before and after a change for each region. Specifically, if at least one of the tube voltage and the beam filter is different during multiple rotational acquisitions, the correction control unit 332 corrects difference between sets of data due to different beam quality.

An explanation is given below, with reference to FIGS. 5 to 7, of correction data if the tube voltage or the beam filter is changed. FIG. 5 is a diagram that illustrates an example of an acquiring by using correction data according to a modified example 5. For example, as illustrated in FIG. 5, the mask image and the first contrast image of the 200 frames are acquired with "the tube voltage: 100 kV", "the tube current: 250 mA", "the pulse width: 12 msec", "the tube focus size: Focus Middle (0.6 mm)", and "the beam filter: Cu 0.2 mm". Conversely, with regard to the second contrast image, the tube voltage and the beam filter are changed, and the second contrast image of 200 frames is acquired with "the tube voltage: 80 kV", "the tube current: 250 mA", "the pulse width: 12 msec", "the tube focus size: Focus Middle (0.6 mm)", and "the beam filter: Al 1.8 mm".

In such a case, the beam quality of X-rays is changed, and the degree of transmission to an object is changed; therefore, instead of a simple linear correction, a correction is performed by using correction data that is generated as illustrated in FIGS. 6 and 7, for example. FIG. 6 is a diagram that illustrates an example of generation of correction data according to the modified example 5. For example, with regard to correction data according to the modified example 5, projection data is first acquired by using the tube voltage and the beam filter before and after a change, as illustrated in FIG. 6. Specifically, as illustrated in (a) of FIG. 6, the projection data "$A_{\theta=0(100, 0.2)}(x, y)$" in a state where nothing is placed and the projection data "$Fe_{\theta=0(100, 0.2)}(x, y)$" in a state where a phantom is placed are acquired under the condition of "the tube voltage: 100 kV" and "the beam filter: Cu 0.2 mm". Here, each set of the above-described projection data is acquired while the rotation angle "θ" is changed. Thus, projection data for the transmission through various thicknesses is acquired.

In the same manner, as illustrated in (β) of FIG. 6, the projection data "$A_{\theta=0(80, 1.8)}(x, y)$" in a state where nothing is placed and the projection data "$F_{\theta=0(80, 1.8)}(x, y)$" in a state where a phantom is placed are acquired under the condition of "the tube voltage: 80 kV" and "the beam filter: Al 1.8 mm". Here, each set of the above-described projection data is also acquired while the rotation angle "0" is changed. To generate correction data, a subtraction is performed by using the following Equation (3) and Equation (4) on the projection data that is acquired with each beam quality as described above, and the values of subtraction data are derived. Here, "α" in Equation (3) represents subtraction data under the condition of "the tube voltage: 100 kV" and "the beam filter: Cu 0.2 mm". Furthermore, "β" in Equation (4) represents subtraction data under the condition of "the tube voltage: 80 kV" and "the beam filter: Al 1.8 mm".

$$\alpha = \log_e \frac{F_{\theta=0(100,0.2)}(x, y)}{A_{\theta=0(100,0.2)}(x, y)} \quad (3)$$

$$\beta = \log_e \frac{F_{\theta=0(80,1.8)}(x, y)}{A_{\theta=0(80,1.8)}(x, y)} \quad (4)$$

Specifically, to generate correction data, as represented by Equation (3) and Equation (4), subtraction data is calculated with respect to each projection angle. Then, to generate correction data, as illustrated in FIG. 7, for example, correction data is generated, in which sets of subtraction data with each beam quality at the same position are related. FIG. 7 is a diagram that illustrates an example of correction data according to the modified example 5.

For example, as illustrated in the upper section of FIG. 7, correction data is generated as a graph in which the vertical axis represents "α", the horizontal axis represents "β", and subtraction data of each position is plotted. Furthermore, the correction data is generated as a graph L1 that is formed by a plural-degree expression by using a least-square method based on the plotted data and, furthermore, a graph L2 is generated which is normalized by using the values of the horizontal axis "P" as illustrated in the lower section of FIG. 7.

For correction data, the graph illustrated in FIG. 7 is generated with all the combinations before and after a change in the beam quality and, furthermore, the graph with all the combinations is generated for each region, such as a chest, abdomen, neck, or pelvic region. Furthermore, in FIG. 6, an explanation is given of a case where the correction data is generated by using a phantom; however, there is no limitation on the embodiment and, for example, there may be a case where it is generated by acquiring projection data while the thickness is gradually changed by using an acrylic board, or the like. Furthermore, there may be a case where a large number of standard CT images are prepared for each region and correction data is generated by simulation.

The correction control unit 332 according to the modified example 5 performs a control so that a correction is performed by using correction data that is generated as described above. For example, if rotational acquisitions are performed under the conditions illustrated in FIG. 5, the correction control unit 332 causes a subtraction operation to be performed on the mask image and the second contrast image that are acquired under the X-ray generation conditions illustrated in FIG. 5 by using the following Equation (5). Here, $DSA_\theta(x, y)$, $MASK_\theta(x, y)$, and $CONT2_\theta(x, y)$ in Equation (5) represent subtraction data, the mask image, and the second contrast image. Furthermore, "θ" in Equation (5) represents the rotation angle. Moreover, "q" in Equation (5) is a correction factor that is determined from correction data.

$$DSA_\theta(x, y) = \log_e \left( -\frac{q^* CONT2_\theta(x, y)}{MASK_\theta(x, y)} \right) \quad (5)$$

For example, if a subtraction operation is performed on a mask image and a contrast image for which at least one of the tube voltage and the beam filter is different, the subtraction operation is performed after the correction control unit 332 performs a correction. For example, as represented by Equation (5), the subtraction unit 23 generates subtraction data on the second contrast image by using the equation in which the second contrast image is multiplied by the correction factor "q". Here, the correction control unit 332 calculates the average value from the correction data with respect to each acquisition direction and uses the calculated average value as the correction factor "q".

Here, there may be a case where the correction factor "q" is determined on a pixel by pixel basis. Specifically, the correction control unit 332 corrects the difference between sets of data due to beam quality on a pixel by pixel basis. In such a case, correction data is generated for each pixel, and the correction control unit 332 performs a control such that a correction is performed by using the generated correction data for each pixel. For example, if rotational acquisitions are performed under the conditions illustrated in FIG. 5, the correction control unit 332 causes a subtraction operation to be performed on the mask image and the second contrast image that are acquired under the X-ray generation conditions illustrated in FIG. 5 by using the following Equation (6).

$$DSA_\theta(x, y) = \log_e\left(-\frac{q(x, y)^* CONT2_\theta(x, y)}{MASK_\theta(x, y)}\right) \quad (6)$$

Specifically, the subtraction unit 23 generates subtraction data on the second contrast image by using the equation in which the second contrast image is multiplied by the correction factor "q(x, y)" on a pixel by pixel basis, as represented by Equation (6).

Furthermore, in the above-described modified example 5, an explanation is given of a case where a correction is performed on projection data; however, there is no limitation on the embodiment, and there may be a case where a correction is performed on reconstructed volume data. In such a case, correction data on volume data is generated in the same manner as the correction data on projection data. Specifically, a reconstruction voxel value with regard to each beam quality is plotted on a graph as illustrated in FIG. 7, a graph is generated which is formed by a plural-degree expression by using a least-square method based on the plotted data, and correction data is generated which is normalized by using the values of the horizontal axis. In the same manner, correction data is generated with respect to all the combinations of the beam qualities. Furthermore, correction data is also generated for each region, such as a chest, abdomen, neck, or pelvic region.

In the above-described first embodiment and the modified examples 1 to 5, an explanation is given of a case where at least one of the tube voltage, the tube current, the pulse width, the X-ray tube focus size, and the beam filter is set for each rotational acquisition. Here, the X-ray generation condition for each rotational acquisition may be previously determined for each acquisition sequence during which multiple rotational acquisitions are performed, or there may be a case where it is set by an operator at the time of acquisition.

As described above, according to the first embodiment, the C-shaped arm 13 supports the X-ray generator 11 and the X-ray detector 12. If rotational acquisitions, which are acquisitions while the C-shaped arm 13 is rotated, are performed multiple times after a contrast agent is injected one time, the condition setting unit 331 sets the generation condition of X-rays that are generated by the X-ray generator 11 for each rotational acquisition. Therefore, the X-ray diagnostic apparatus 1 according to the first embodiment can change the X-ray generation condition for each rotational acquisition and can acquire the optimum image data during each rotational acquisition.

For example, when rotational acquisitions are performed twice after a contrast agent is injected, if a signal acquired during the second acquisition is extremely weaker than a signal acquired during the first acquisition, the X-ray diagnostic apparatus 1 increases the amount of X-rays during the second acquisition; thus, it is possible to eliminate a shortage of the dose and to provide an image by which the object of interest can be correctly observed. Furthermore, for example, when rotational acquisitions are performed twice after a contrast agent is injected, if the region of interest during the first acquisition has a detailed structure while the region of interest during the second acquisition has a rough structure, the X-ray diagnostic apparatus 1 reduces the amount of X-rays during the second acquisition; thus, it is possible to prevent an unnecessary dose and to provide an image by which the object of interest can be correctly observed.

Furthermore, according to the first embodiment, the condition setting unit 331 sets, for each rotational acquisition, at least one of the tube voltage, the tube current, the pulse width, the X-ray tube focus size, and the beam filter as the X-ray generation condition. Therefore, the X-ray diagnostic apparatus 1 according to the first embodiment can change the details of the X-ray generation condition for each rotational acquisition.

Furthermore, according to the first embodiment, the correction control unit 332 corrects data that is acquired by the X-ray detector 12 in accordance with the X-ray generation condition that is set by the condition setting unit 331. Therefore, the X-ray diagnostic apparatus 1 according to the first embodiment can display the accurate display image.

Furthermore, according to the first embodiment, if a subtraction operation is performed by using a mask image and a contrast image that are acquired under different generation conditions, the correction control unit 332 corrects those projection data such that the subtraction operation is performed on the sets of projection data for which the generation conditions are matched. In other words, when a subtraction operation is performed by using projection data of a mask image and projection data of a contrast image that are acquired under different generation conditions, the correction control unit 332 corrects at least one of the projection data of the mask image and the projection data of the contrast image such that the subtraction operation is performed by using sets of projection data for which the generation conditions are matched. Therefore, the X-ray diagnostic apparatus 1 according to the first embodiment can properly perform a correction.

Furthermore, according to the first embodiment, if a subtraction operation is performed by using reconstruction data that are reconstructed from a mask image and a contrast image that are acquired under different generation conditions, the correction control unit 332 corrects the reconstruction data such that the subtraction operation is performed on the sets of reconstruction data for which the generation conditions are matched. In other words, when a subtraction operation is performed by using reconstruction data that is reconstructed from projection data of a mask image and reconstruction data that is reconstructed from projection data of a contrast image that are acquired under different generation conditions, the correction control unit 332 corrects at least one of the reconstruction data that is reconstructed from the projection data of the mask image and the reconstruction data that is reconstructed from the projection data of the contrast image such that the subtraction operation is performed by using sets of reconstruction data for which the generation conditions are matched. Therefore, the X-ray diagnostic apparatus 1 according to the first embodiment can remove artifacts due to misregistration.

Furthermore, according to the first embodiment, if there is a difference in at least one of the tube voltage and the beam filter during multiple rotational acquisitions, the correction control unit 332 corrects the difference between sets of data due to different beam quality. Therefore, the X-ray diagnostic apparatus 1 according to the first embodiment can handle with a change in the X-ray generation condition by which the beam quality is changed.

Furthermore, according to the first embodiment, the correction control unit 332 corrects the difference between sets of data due to the degree of hardness on a pixel by pixel basis. Therefore, the X-ray diagnostic apparatus 1 according to the first embodiment can perform a correction with higher accuracy.

Furthermore, according to the first embodiment, the display control unit 333 causes the display unit 40 to display multiple three-dimensional images that are taken during rotational acquisitions under the X-ray generation conditions that are set by the condition setting unit 331. Therefore, the X-ray diagnostic apparatus 1 according to the first embodiment can display an easily observable image with regard to the images taken during multiple rotational acquisitions.

Furthermore, according to the first embodiment, the display control unit 333 fuses multiple three-dimensional images for a display. Therefore, the X-ray diagnostic apparatus 1 according to the first embodiment makes it possible to instantly check the positional relationship between the objects that are captured during different time phases.

Furthermore, according to the first embodiment, the display control unit 333 causes multiple three-dimensional images to be displayed in different colors. Therefore, the X-ray diagnostic apparatus 1 according to the first embodiment makes it possible to instantly check each object.

Furthermore, according to the first embodiment, a three-dimensional image is a volume rendering image or an MPR image. Therefore, the X-ray diagnostic apparatus 1 according to the first embodiment can display the object that is taken during a rotational acquisition as various three-dimensional images.

Second Embodiment

Although the first embodiment is explained above, various different embodiments other than the above-described first embodiment may be implemented.

Figure 8:
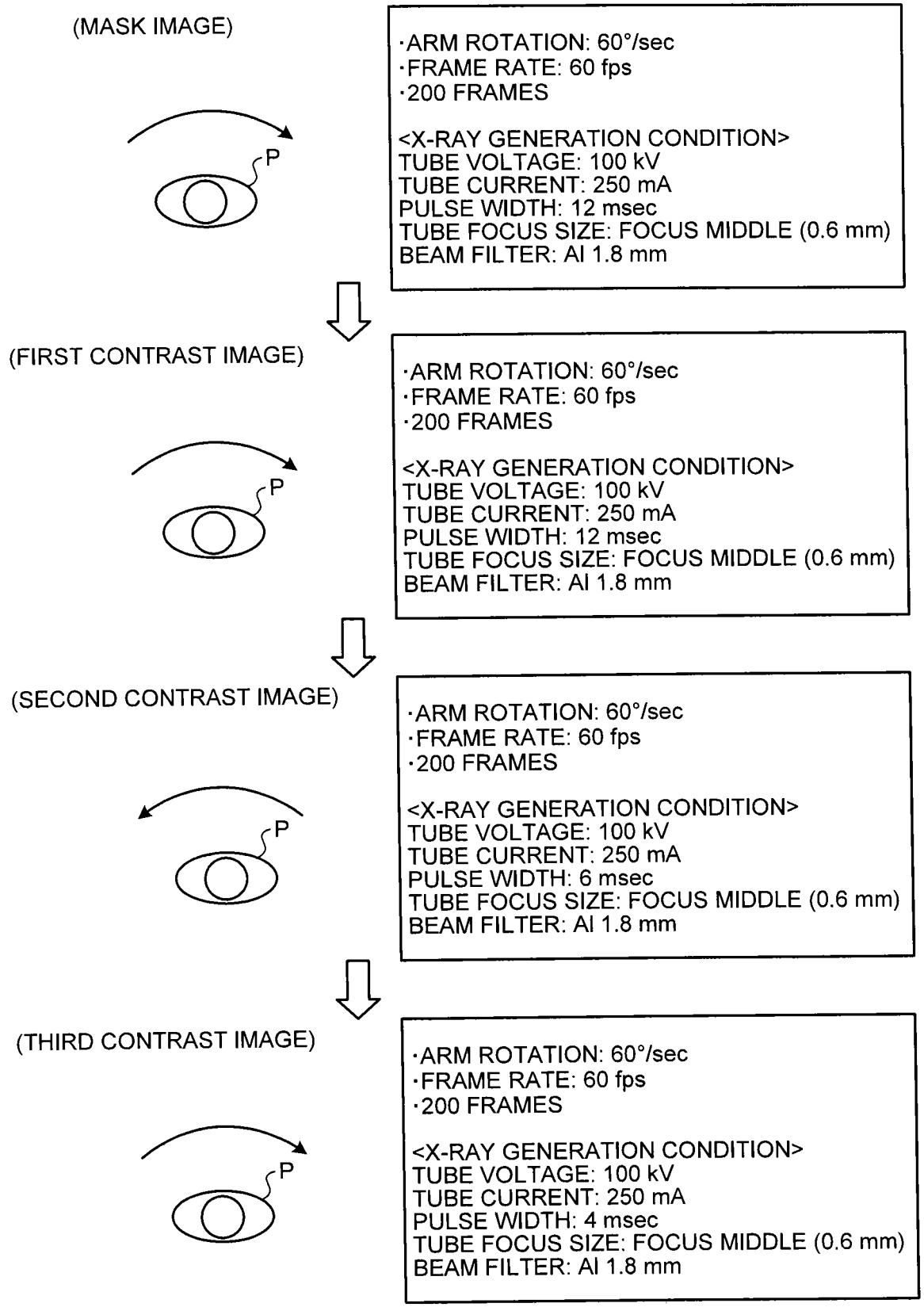
FIG. 8 is a diagram that illustrates an example of a rotational acquisition of the X-ray diagnostic apparatus according to a second embodiment.

In the above-described first embodiment, an explanation is given of a case where rotational acquisitions are performed twice after a contrast agent is injected. However, there is no limitation on the embodiment and, for example, there may be a case where rotational acquisitions are performed three times or more. FIG. 8 is a diagram that illustrates an example of a rotational acquisition of the X-ray diagnostic apparatus according to a second embodiment. FIG. 8 illustrates a case where a rotational acquisition is performed once more after the rotational acquisitions illustrated in FIG. 3. Specifically, FIG. 8 illustrates, for example, a case where the mask image and the first contrast image are acquired under the same X-ray generation condition, the pulse width of X-rays that are generated by the X-ray generator 11 is changed for the second contrast image, and the pulse width is further changed for the third contrast image.

For example, in the X-ray diagnostic apparatus 1, as illustrated in FIG. 8, after the acquisition illustrated in FIG. 3, the second contrast image is acquired and then, after a specific time (the time that is different from the first and the second times) further elapses from the start of imaging, the C-shaped arm 13 is rotated (forward) 60 degrees per second (arm rotation: 60°/sec), the projection angle is changed at a fixed frame rate (frame rate: 60 fps), and the third contrast image of 200 frames is acquired at an interval of 1 degree. Here, the condition setting unit 331 changes the X-ray generation condition to acquire the third contrast image. For example, the condition setting unit 331 changes "the pulse width" from "6 msec" to "4 msec" to capture the third contrast image. Specifically, the acquisition control unit 27 causes the third contrast image of 200 frames to be acquired with "the tube voltage: 100 kV", "the tube current: 250 mA", "the pulse width: 4 msec", "the tube focus size: Focus Middle (0.6 mm)", and "the beam filter: Al 1.8 mm". The acquired third contrast image of 200 frames is converted into digital signals by the A/D conversion unit 21 and is stored in the image memory 22.

For example, if "the pulse width" is changed like the third contrast image of FIG. 8, the correction control unit 332 causes a subtraction operation to be performed on the mask image and the third contrast image by using the following Equation (7). Here, $DSA_\theta(x, y)$, $MASK_\theta(x, y)$, and $CONT3_\theta(x, y)$ in Equation (7) represent subtraction data, the mask image, and the third contrast image. Furthermore, "$\theta$" in Equation (7) represents the rotation angle. Moreover, a subtraction operation is performed on the first contrast image and the second contrast image by using the same equation as that in the first embodiment.

$$DSA_\theta(x, y) = \log_e\left(-\frac{3 \times CONT3_\theta(x, y)}{MASK_\theta(x, y)}\right) \quad (7)$$

For example, as illustrated in FIG. 8, if a subtraction is performed on the mask image acquired with "the pulse width: 12 msec" and the third contrast image acquired with "the pulse width: 4 msec", the subtraction unit 23 generates subtraction data on the third contrast image by using the equation in which the third contrast image is multiplied by the correction factor "3" as represented by Equation (7). Specifically, the subtraction unit 23 reads, from the image memory 22, 200 frames of the mask image and 200 frames of the third contrast image and performs a subtraction on the sets of projection data of a corresponding rotation angle by using Equation (7), thereby generating subtraction data on the third contrast image.

As described above, after sets of subtraction data on the first contrast image, the second contrast image, and the third contrast image are generated, the three-dimensional reconstruction unit 31 reconstructs volume data from each set of subtraction data, and the three-dimensional image processing unit 32 generates a three-dimensional image from each set of reconstructed volume data. Then, the display control unit 333 causes the display unit 40 to display the generated three-dimensional image. Furthermore, if rotational acquisitions are performed three times or more as described above, each of the operations according to the modified examples 1 to 5 of the above-described first embodiment can be performed.

An explanation is given above of an example of the operation of the X-ray diagnostic apparatus 1 according to the second embodiment. In the above-described example, an explanation is given of a case where the pulse width for acquiring the third contrast image is narrower than the pulse width for acquiring the second contrast image and the pulse width for acquiring the second contrast image is narrower than the pulse width for acquiring the first contrast image. This embodiment is applied to acquiring of, for example, hepatic arteries or arteries of the brain. For example, proper hepatic arteries, internal carotid arteries, vertebral arteries, or the like, are acquired with the first contrast image, hepatic veins, capillary blood vessels, or the like, are acquired with the second contrast image, and corona enhancement or veins of the brain are acquired with the third contrast image.

In the above-described embodiment, an explanation is given of a case where the amount of X-rays is changed by changing the pulse width; however, there is no limitation on the embodiment, and there may be a case where the amount of X-rays is changed by changing the tube current. Furthermore, there may be a case where each of the tube current and the pulse width is changed.

In the above-described embodiment, an explanation is given of a case where one or two of the tube voltage, the tube current, the pulse width, the X-ray tube focus size, and the beam filter is changed. However, there is no limitation on the embodiment, and there may be a case where a change is made to any combination of them. In such a case, a combination of the above-described corrections is performed.

In the above-described embodiment, an explanation is given of a case where the X-ray generation condition is set as an imaging condition for each rotational acquisition; however, there is no limitation on the embodiment. For example, the required image quality level is related to the function for a reconstruction. Therefore, an image reconstruction condition may be set as an imaging condition for a case of a reconstruction of subtraction data on the first contrast image and for a case of a reconstruction of subtraction data on the second contrast image. Specifically, during rotational acquisitions that are performed multiple times, the condition setting unit 331 further changes a reconstruction condition in accordance with the purpose of the rotational acquisition. Then, the three-dimensional reconstruction unit 31 reconstructs an image under the reconstruction condition that corresponds to the required image quality level.

For example, an image quality level of veins of a cephalic region is low; therefore, if they are processed by using a high-pass filter as is the case with arteries, noise is increased. Therefore, during rotational acquisitions that are performed multiple times, when the rotational acquisition is performed for an image from which a venous phase is extracted and an image from which an arterial phase is extracted, the condition setting unit 331 sets a reconstruction condition to reconstruct the image from which a venous phase is extracted by using a weakened high-pass filter compared to the case of a reconstruction of the image from which an arterial phase is extracted. Then, when veins of a cephalic region are reconstructed, the three-dimensional reconstruction unit 31 performs an operation by using a weakened high-pass filter compared to the case of a reconstruction of arteries, whereby noise is reduced. Furthermore, as contrast-agent density information with regard to a capillary blood vessel image is generally extremely little, if a reconstruction is performed in the same manner as arteries, noise is increased. Therefore, during rotational acquisitions that are performed multiple times, if the rotational acquisition is performed for an image from which a capillary blood vessel phase is extracted and an image from which a venous phase is extracted, the condition setting unit 331 sets a reconstruction condition to reconstruct the image from which a capillary blood vessel phase is extracted by using a weakened high-pass filter compared to the case of a reconstruction of the image from which a venous phase is extracted. Then, in the case of a reconstruction of capillary blood vessels, the three-dimensional reconstruction unit 31 performs an operation by using a weakened high-pass filter compared to the case of a reconstruction of veins, whereby noise is reduced.

Furthermore, for example, in the case of an identification of a hepatocellular tumor in an early stage, the condition setting unit 331 sets a reconstruction condition that is different from that in the case of an identification of a hepatocellular tumor in a middle stage or a hepatocellular tumor in a late stage. Here, a hepatocellular tumor has stages, and the contrast during the contrast enhancement is changed from a hepatocellular tumor in an early stage to a hepatocellular tumor in a middle stage and then a hepatocellular tumor in a late stage. For example, in the case of a hepatocellular tumor in an early stage, the contrast enhancement is not different from that of normal hepatic cells, and the contrast is low. Specifically, with regard to a hepatocellular tumor in an early stage, low-contrast information is dominant. For this reason, during rotational acquisitions that are performed multiple times, when the rotational acquisition is performed for an image from which a hepatocellular tumor in an early stage is extracted and an image from which a hepatocellular tumor in a middle stage or a hepatocellular tumor in a late stage is extracted, the condition setting unit 331 sets a reconstruction condition to reconstruct the image from which a hepatocellular tumor in an early stage is extracted by using a weakened high-pass filter compared to the case of a reconstruction of the image from which a hepatocellular tumor in a middle stage or a hepatocellular tumor in a late stage is extracted. Then, the three-dimensional reconstruction unit 31 performs an operation by using a weakened high-pass filter compared to the case of a reconstruction of a hepatocellular tumor in a middle stage or a hepatocellular tumor in a late stage, whereby noise is reduced. Furthermore, the X-ray generation condition for acquiring a hepatocellular tumor in an early stage is set such that the amount of X-rays is increased as is the case with the X-ray generation condition for acquiring a hepatocellular tumor in a middle stage or a hepatocellular tumor in a late stage. Specifically, to identify a hepatocellular tumor in an early stage or a hepatocellular tumor in a middle and subsequent stage, the reconstruction conditions are different although the X-ray generation conditions are the same.

Furthermore, in the above-described embodiment, an explanation is given of a case where, after a mask image is acquired, the C-shaped arm 13 is rotated in reverse and is returned to a rotation start position; however, there is no limitation on the embodiment. For example, after a mask image is acquired, the C-shaped arm 13 may be rotated in reverse so that the first contrast image is acquired.

Another Embodiment

Figure 9:
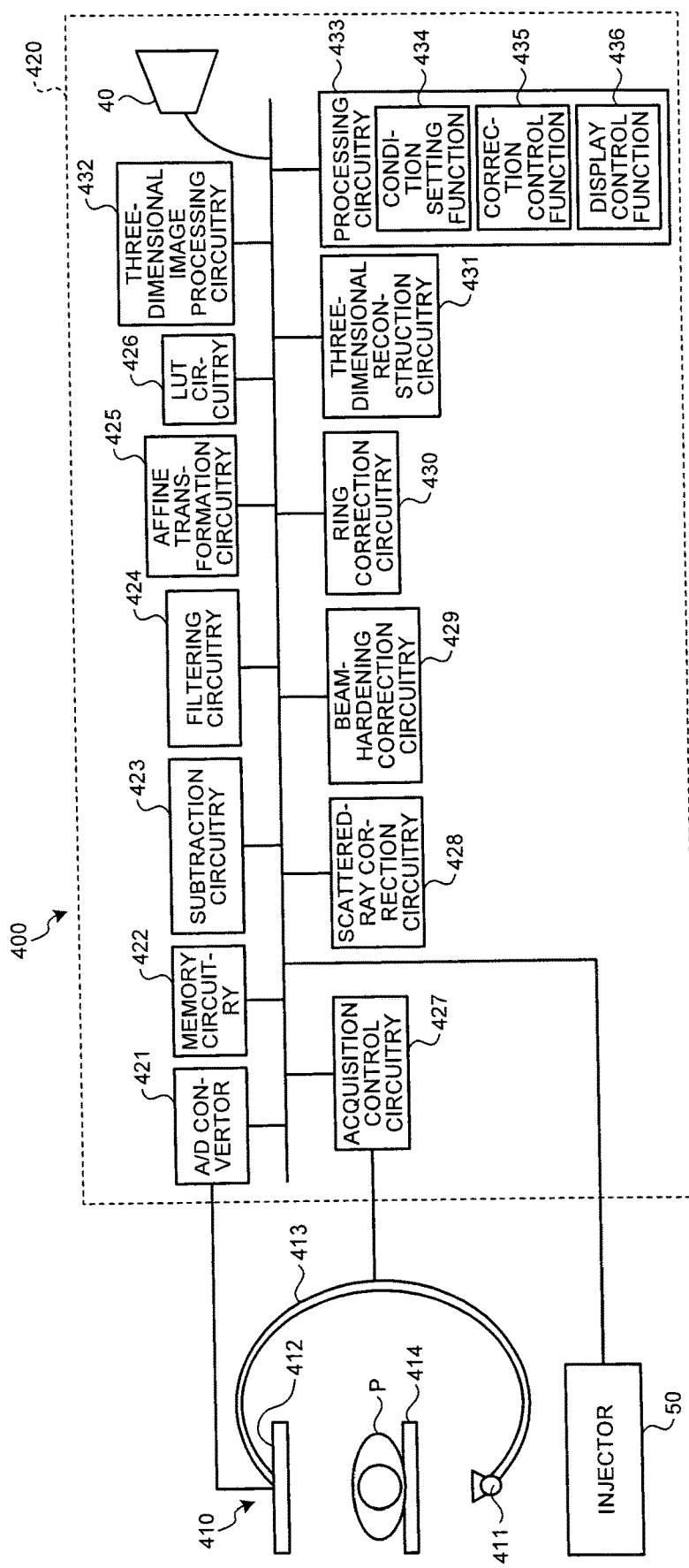
FIG. 9 is a diagram that illustrates an example of the configuration of an X-ray diagnostic apparatus according to another embodiment.

The X-ray diagnostic apparatus illustrated in the description of the first embodiment and the second embodiment may be configured as illustrated in FIG. 9, for example. FIG. 9 is a diagram that illustrates an example of the configuration of an X-ray diagnostic apparatus 400 according to another embodiment.

As illustrated in FIG. 9, the X-ray diagnostic apparatus 400 according to the other embodiment includes an X-ray acquisition mechanism 410 and an image processing device 420. The X-ray acquisition mechanism 410 and the image processing device 420 correspond to the X-ray acquisition mechanism 10 and the image processing device 100 illustrated in FIG. 1, respectively.

As illustrated in FIG. 9, the X-ray acquisition mechanism 410 includes an X-ray generator 411, an X-ray detector 412, a C-shaped arm 413, and a bed 414, and the X-ray acquisition mechanism 410 is connected to an injector 50. The X-ray generator 411, the X-ray detector 412, the C-shaped arm 413, and the bed 414 illustrated in FIG. 9 correspond to the X-ray generator 11, the X-ray detector 12, the C-shaped arm 13, and the bed 14 illustrated in FIG. 1, respectively.

As illustrated in FIG. 9, the image processing device 420 includes an A/D converter 421, storage circuitry 422, subtraction circuitry 423, filtering circuitry 424, affine transformation circuitry 425, LUT circuitry 426, acquisition control circuitry 427, scattered-ray correction circuitry 428, beam-hardening correction circuitry 429, ring correction circuitry 430, three-dimensional reconstruction circuitry 431, three-dimensional image processing circuitry 432, processing circuitry 433, and a display 40.

The A/D converter 421 corresponds to the A/D conversion unit 21 illustrated in FIG. 1, and the storage circuitry 422 corresponds to the image memory 22 illustrated in FIG. 1. The subtraction circuitry 423 corresponds to the subtraction unit 23 illustrated in FIG. 1 and performs the processing at Step S106 illustrated in FIG. 2. The filtering circuitry 424, the affine transformation circuitry 425, and the LUT 426 correspond to the filtering unit 24, the affine transformation unit 25, and the LUT 26 illustrated in FIG. 1, respectively. The acquisition control circuitry 427 corresponds to the acquisition control unit 27 illustrated in FIG. 1 and performs the processing at Step S101, Step S103, and Step S105 illustrated in FIG. 2. The scattered-ray correction circuitry 428, the beam-hardening correction circuitry 429, and the ring correction circuitry 430 correspond to the scattered-ray correction unit 28, the beam-hardening correction unit 29, and the ring correction unit 30 illustrated in FIG. 1, respectively. The three-dimensional reconstruction circuitry 431 corresponds to the three-dimensional reconstruction unit 31 illustrated in FIG. 1 and performs the processing at Step S107 illustrated in FIG. 2. The three-dimensional image processing circuitry 432 and the display 40 correspond to the three-dimensional image processing unit 32 and the display unit 40 illustrated in FIG. 1, respectively.

The processing circuitry 433 corresponds to the control unit 33 illustrated in FIG. 1 and performs a condition setting function 434, a correction control function 435, and a display control function 436. The processing circuitry 433 is an example of processing circuitry described in the Claims. The condition setting function 434 is a function implemented by the condition setting unit 331 illustrated in FIG. 1. The correction control function 435 is a function implemented by the correction control unit 332 illustrated in FIG. 1. The display control function 436 is a function implemented by the display control unit 333 illustrated in FIG. 1.

For example, each of the respective processing functions performed by the condition setting function 434, the correction control function 435, and the display control function 436, which are components of the processing circuitry 433 illustrated in FIG. 9, is stored in the storage circuitry 422 in a form of a computer-executable program. The processing circuitry 433 is a processor that loads programs from the storage circuitry 422 and executes the programs so as to implement the respective functions corresponding to the programs. In other words, the processing circuitry 433 that has loaded the programs has the functions illustrated in the processing circuitry 433 in FIG. 9. That is, the processing circuitry 433 loads a program corresponding to the condition setting function 434 from the storage circuitry 422 and executes the program so as to perform the same processing as that of the condition stetting unit 331. The processing circuitry 433 loads a program corresponding to the correction control function 435 from the storage circuitry 422 and executes the program so as to perform the same processing as that of the correction control unit 332. The processing circuitry 433 loads a program corresponding to the display control function 436 from the storage circuitry 422 and executes the program so as to perform the same processing as that of the display control unit 333.

For example, Step S105 illustrated in FIG. 2 is a step that is implemented by the processing circuitry 433 loading the program corresponding to the condition setting function 434 from the storage circuitry 422 and executing the program.

Step S108 illustrated in FIG. 2 is a step that is implemented by the processing circuitry 433 loading the program corresponding to the display control function 436 from the storage circuitry 422 and executing the program.

In FIG. 9, the processing functions performed by the condition setting function 434, the correction control function 435, and the display control function 436 are described as being implemented in the single processing circuitry 433. The functions, however, may be implemented by configuring processing circuitry by combining a plurality of separate processors and causing each of the processors to execute a program.

The term "processor" used in the above description means, for example, a central preprocess unit (CPU) and a graphics processing unit (GPU), or circuitry such as an application specific integrated circuit (ASIC), a programmable logic device (for example, a simple programmable logic device (SPLD)), a complex programmable logic device (CPLD), and a field programmable gate array (FPGA). The processor implements a function by loading and executing a program stored in storage circuitry. Instead of being stored in storage circuitry, the program may be built directly in circuitry of the processor. In this case, the processor implements a function by loading and executing the program built in the circuitry. The processors in the present embodiment are not limited to a case in which each of the processors is configured as a single circuit. A plurality of separate circuits may be combined as one processor that implements the respective functions. Furthermore, the components illustrated in FIG. 9 may be integrated into one processor that implements the respective functions.

As described above, according to the first embodiment and the second embodiment, the X-ray diagnostic apparatus of the embodiment can acquire the optimum image data for each rotational acquisition.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
a C-arm that supports an X-ray generator at one end and an X-ray detector at another end; and
processing circuitry configured to, when a rotational acquisition is performed multiple times after a contrast agent is injected one time, previously set an X-ray dosage per unit area as a generation condition of an X-ray that is generated by the X-ray generator for a first rotational acquisition and a second rotational acquisition, respectively, the first rotational acquisition being performed while the C-arm is rotated around a subject in a first rotation direction, the second rotational acquisition being performed while the C-arm is rotated around the subject in a second rotation direction that is opposite to the first rotation direction,
wherein the processing circuitry is further configured to control the first rotational acquisition and the second rotational acquisition to acquire projection data of a substantially identical region of the subject in an identical circular orbit by controlling the C-arm to rotate back and forth along the identical circular orbit during multiple rotational acquisitions.

2. The X-ray diagnostic apparatus according to claim 1, wherein the first rotational acquisition and the second rotational acquisition are automatically performed after the contrast agent is injected once.

3. The X-ray diagnostic apparatus according to claim 1, wherein, when at least one of the first rotational acquisition and the second rotational acquisition is performed on a capillary blood vessel phase or a venous phase of the subject, the processing circuitry is further configured to set the generation condition of the X-ray such that an amount of X-rays is decreased compared to other phases.

4. The X-ray diagnostic apparatus according to claim 1, wherein, when at least one of the first rotational acquisition and the second rotational acquisition is performed on an arterial phase of the subject, the processing circuitry is further configured to set the generation condition of the X-ray such that an amount of X-rays is increased compared to other phases.

5. The X-ray diagnostic apparatus according to claim 1, wherein the processing circuitry is further configured to set at least one of a tube voltage, a tube current, a pulse width, an X-ray tube focus size, and a beam filter for the first rotational acquisition and the second rotational acquisition, respectively.

6. The X-ray diagnostic apparatus according to claim 1, wherein the processing circuitry is further configured to correct data that is acquired by the X-ray detector in accordance with the generation condition of the X-ray that is set by the processing circuitry.

7. The X-ray diagnostic apparatus according to claim 6, wherein when a subtraction operation is performed by using projection data of a mask image and projection data of a contrast image that are acquired under different generation conditions, the processing circuitry is further configured to correct at least one of the projection data of the mask image and the projection data of the contrast image such that the subtraction operation is performed by using sets of projection data for which the generation conditions are matched.

8. The X-ray diagnostic apparatus according to claim 6, wherein the processing circuitry is further configured to reconstruct three-dimensional mask reconstruction data from projection data of a mask image, reconstruct three-dimensional contrast reconstruction data from projection data of a contrast image, and perform a subtraction operation by using the three-dimensional mask reconstruction data and the three-dimensional contrast reconstruction data.

9. The X-ray diagnostic apparatus according to claim 6, wherein, when at least one of the tube voltage and the beam filter is different during the first rotational acquisition and the second rotational acquisition, the processing circuitry is further configured to correct a difference between sets of data due to beam quality.

10. The X-ray diagnostic apparatus according to claim 9, wherein the processing circuitry is further configured to correct the difference between sets of data due to the beam quality on a pixel by pixel basis.

11. The X-ray diagnostic apparatus according to claim 1, wherein the processing circuitry is further configured to cause a display to display multiple three-dimensional images that are taken during the first rotational acquisition and the second rotational acquisition under X-ray generation conditions that are set by the processing circuitry.

12. The X-ray diagnostic apparatus according to claim 11, wherein the processing circuitry is further configured to display the multiple three-dimensional images in fusion.

13. The X-ray diagnostic apparatus according to claim 12, wherein the processing circuitry is further configured to display the three-dimensional images in different colors.

14. The X-ray diagnostic apparatus according to claim 12, wherein the three-dimensional images are volume rendering images or MPR images.

15. The X-ray diagnostic apparatus according to claim 1, wherein, during the multiple rotational acquisitions, the processing circuitry is further configured to change a reconstruction condition in accordance with a purpose of each rotational acquisition.

16. The X-ray diagnostic apparatus according to claim 15, wherein, when at least one of the first rotational acquisition and the second rotational acquisition is performed for an image from which a venous phase is extracted and an image from which an arterial phase is extracted, the processing circuitry is further configured to set a reconstruction condition to reconstruct the image from which the venous phase is extracted by using a weakened high-pass filter compared to a case of a reconstruction of the image from which the arterial phase is extracted.

17. The X-ray diagnostic apparatus according to claim 15, wherein, when at least one of the first rotational acquisition and the second rotational acquisition is performed for an image from which a hepatocellular tumor in an early stage is extracted and an image from which a hepatocellular tumor in a middle stage or a hepatocellular tumor in a late stage is extracted, the processing circuitry is further configured to set a reconstruction condition to reconstruct the image from which a hepatocellular tumor in an early stage is extracted by using a weakened high-pass filter compared to a case of a reconstruction of the image from which a hepatocellular tumor in a middle stage or a hepatocellular tumor in a late stage is extracted.

18. The X-ray diagnostic apparatus according to claim 1, wherein the processing circuitry is further configured to perform a rotational acquisition for taking mask images before the contrast agent is injected, and when a rotational acquisition is performed multiple times for taking contrast images after the contrast agent is injected one time, perform at least one of rotational acquisitions for taking contrast images by using a generation condition of an X-ray to be different from a generation condition used by the other rotational acquisition.

19. The X-ray diagnostic apparatus according to claim 1, wherein the first rotational acquisition and the second rotational acquisition start at a corresponding predetermined elapsed time from a base time, respectively.

20. The X-ray diagnostic apparatus according to claim 1, wherein the processing circuitry is further configured to set the generation condition of the X-ray such that, out of the multiple rotational acquisitions, a total amount of X-ray radiation during the second rotational acquisition that is performed after the first rotational acquisition is nearly equal to or more than twice or nearly equal to or less than ½ of a total amount of X-ray radiation during the first rotational acquisition.

* * * * *